(12) United States Patent
Tuffin et al.

(10) Patent No.: US 6,436,312 B1
(45) Date of Patent: Aug. 20, 2002

(54) LIQUID CRYSTAL COMPOSITION AND LIQUID CRYSTAL SHUTTER

(75) Inventors: Rachel Patricia Tuffin; Andrew John Slaney; John Clifford Jones, all of Worcestershire (GB); Mitsuhiro Koden, Kashiwa (JP)

(73) Assignees: Sharp Kabushiki Kaisha, Osaka (JP); The Secretary of State for Defence in Her Britannic Majesty's Government of the United Kingdom of Great Britian and Northern Ireland, DRA Farnborough (GB)

( * ) Notice: Subject to any disclaimer, the term of this patent is extended or adjusted under 35 U.S.C. 154(b) by 0 days.

(21) Appl. No.: 09/548,765

(22) Filed: Apr. 13, 2000

(30) Foreign Application Priority Data

Apr. 14, 1999 (GB) .............................................. 9908362

(51) Int. Cl.$^7$ ........................ C09K 19/12; C09K 19/52; C07C 69/76; C07C 25/13
(52) U.S. Cl. ........................... 252/299.01; 252/299.66; 560/65; 570/129
(58) Field of Search ..................... 252/299.01, 299.66, 252/299.67; 560/65; 570/129

(56) References Cited

U.S. PATENT DOCUMENTS 5,279,764 A * 1/1994 Reiffenrath et al. ..... 252/299.66
6,151,093 A * 11/2000 Takiguchi et al. .......... 349/172

* cited by examiner

Primary Examiner—Shean C. Wu
(74) Attorney, Agent, or Firm—Renner, Otto, Boisselle & Sklar, LLP

(57) ABSTRACT

A liquid crystal composition comprises a host material capable of exhibiting a smectic C phase, and a chiral dopant material which imparts or enhances chirality in the host material. The composition exhibits $\tau\text{-}V_{min}$ curves. The chiral dopant material comprises at least first and second chiral centers. The chiral centers individually produce, in the liquid crystal composition, different and complementary temperature coefficients of spontaneous polarization within a predetermined temperature range. The chiral centers are present in the liquid crystal composition in relative amounts such that regions of the $\tau\text{-}V_{min}$ curves across the predetermined temperature range are substantially coincident.

10 Claims, 7 Drawing Sheets

LIQUID CRYSTAL COMPOSITION AND LIQUID CRYSTAL SHUTTER

BACKGROUND TO THE INVENTION

The present invention relates to a liquid crystal composition and a liquid crystal shutter arrangement containing such a composition, for example a liquid crystal display device including a multiplicity of liquid crystal shutters.

Ferroelectric liquid crystal compositions suitable for fast, high-contrast displays with high levels of multiplexing and wide operating ranges are known (see for example J. C. Jones et al, *Ferroelectrics,* 1991, Vol. 121, pp91–102, and J. C. Jones et al, *Displays, Vol.* 14, No. 2, 1993, pp 86–93) which exhibit response time($\tau$)-operating voltage (V) curves having a minimum ($\tau$-$V_{min}$ curves) when operated with pulsed switching drive schemes. Such compositions have significant dielectric biaxialities and relatively low values of the spontaneous polarisation Ps. The viscosity of these compositions increases with decreasing temperature. However, the spontaneous polarisation Ps of the liquid crystal molecules generally increases with decreasing temperature T (see FIG. 10), but the corresponding increase in speed of switching is insufficient to overcome the effect of increased viscosity. The result of this is that the $\tau$-$V_{min}$ curves of these compositions are temperature-dependent (see FIG. 11). Thus, the operating voltage signal required to switch the state of the liquid crystals changes with temperature. Accordingly, the required switching of the display may fail to take place at some temperatures encountered in use. In the case of global temperature changes, i.e. where the temperature of the whole display changes more or less uniformly, this can be at least partly compensated for varying the operating voltage signal depending upon the temperature of the display, or by controlling the temperature of the display. However, neither of these measures represents an ideal solution and does not easily permit temperature compensation where parts of the display are at different temperatures.

Additionally, problems also arise with analogue greyscale devices, where not only white and black are to be displayed, but also intermediate greys. In such devices, it is even more important than in digital white/black displays to reduce the temperature-dependence of the switching characteristics.

It is an object of the present invention to provide an improved liquid crystal composition which can enable the above problem to be obviated or mitigated.

SUMMARY OF THE INVENTION

According to a first aspect of the present invention, there is provided a liquid crystal composition comprising a host material capable of exhibiting a smectic C phase, and a chiral dopant material which imparts or enhances chirality in the host material, said composition exhibiting temperature-dependent response time-voltage curves with a voltage minimum ($\tau$-$V_{min}$ curves), wherein (a) the chiral dopant material has at least two chiral centres, (b) the chiral centres individually produce, in the liquid crystal composition, different and complementary temperature coefficients of spontaneous polarisation within a predetermined temperature range, and (c) the chiral centres are present in the liquid crystal composition in relative amounts such that regions of the $\tau$-$V_{min}$ curves across the predetermined temperature range are substantially coincident.

The chiral centres may be provided as chiral moieties in one or more chiral dopants.eg in a single chiral dopant compound or in different chiral dopant compounds.

The predetermined temperature range is typically a range of at least 20° C., and preferably 20 to 40° C.

The required variation of spontaneous polarisation with temperature in a liquid crystal composition according to the present invention is shown in FIG. 12. An inversion point (see the dotted line) may or may not be present. FIG. 13 illustrates a possible case where two dopants A and B separately produce different Ps curves ($Ps_A$ and $Ps_B$, respectively), whilst the use of these two dopants together produces a Ps curve ($Ps_{(A+B)}$) which is proportional to the sum of the squares of $Ps_A$ and $Ps_B$, or which is proportional to $Ps_A + Ps_B + 2Ps_A Ps_B$, ie a non-linear addition of Ps.

The result sought in a liquid crystal composition according to the present invention is substantial overlapping of the $\tau$-$V_{min}$ curves for substantially all temperatures within an operating temperature range ($T_1$ to $T_2$) of a device incorporating such a composition (see FIG. 14) so as to allow addressing of the device using the same voltage and addressing time at any temperature within such range.

The total amount of chiral dopant material may be up to about 25% based on the total weight of the liquid composition, and is more usually 2 to 10 wt %, and preferably is about 2 to 5%.

The first chiral centre may exhibit a spontaneous polarisation having an opposite sign to that of the second chiral centre.

In the case where the spontaneous polarisation of a liquid crystal composition containing the first and second chiral centres is too low for fast switching to occur, at least one further chiral centre having a relatively high temperature coefficient of spontaneous polarisation can be included so as to increase the spontaneous polarisation of the resultant liquid crystal composition and yet not have too great an effect on the overall temperature coefficient of spontaneous polarisation of the composition. An example of such a further chiral centre is that in a dopant has the following formula (I):

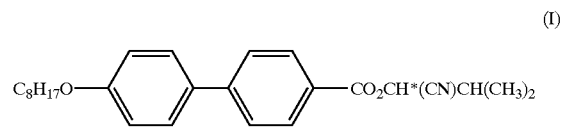

(I)

Either chiral form of such dopant may be utilised (see dopants (VIII) and (IX) below).

The first chiral centre may be provided by a first chiral dopant having a lactate moiety in the chiral region. Examples of these are the compounds having the following formulae (II) and (III):

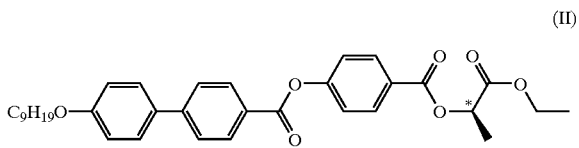

(II)

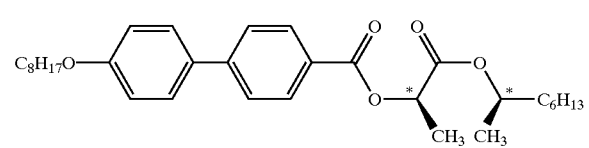

(III)

Other examples of first chiral dopant are fluoroterphenyl compounds having a chiral centre in an end group of the molecule. An example of this is a compound of the following formula (IV):

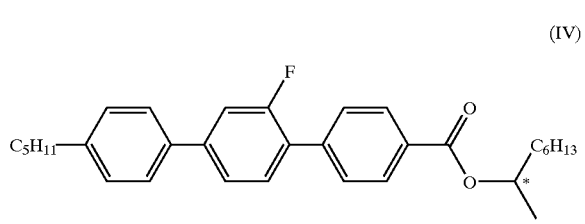

(IV)

The above first dopants typically have a relatively low temperature coefficient (γ) of spontaneous polarisation.

With regard to the second chiral moiety, this preferably has a relatively high γ. The second chiral moiety may be provided by a second chiral dopant based on a Bahr-Heppke C-series type compound [for example, compound (V)] wherein a biphenyl compound has a branched chain alkyl-carbonyloxy substituent group which is halo-substituted (typically chlorine) at the chiral centre. The biphenyl group in such dopant may be fluoro-substituted, preferably difluoro-substituted, on the phenyl ring which is closest to the chiral centre. Typical examples are those of the formulae (V) and (VI):

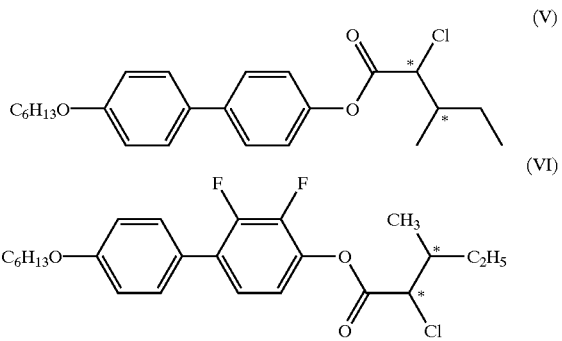

The compound (VI) is believed to be novel. Thus, the present invention also relates to said compound (VI) per se.

In the case where the chiral dopant material comprises a compound of the formula (III) as the first chiral dopant and a compound of the formula (V) as the second chiral dopant, it is preferred for these dopants to be present in approximately equal proportions by weight.

In the case where the chiral dopant material comprises a dopant of the formula (III) and a dopant of the formula (VI), it is also preferred for these two dopants to be present in the liquid crystal composition in approximately equal quantities by weight.

The particular combinations of the first and second chiral centres (and the further chiral centre when present) required to produce the best effect are of course dependent upon the nature of the host material. The host material is normally a mixture of compounds capable of exhibiting phase changes upon cooling so that the composition passes from the isotropic phase (I) through chiral nematic (N*) and smectic A (SmA) phases before reaching the operative smectic C* phase. This is referred to as an I-N*-SmA-SmC* phase sequence.

As far as the host material is concerned, one type of host material is based on a mixture of diphenyl-carbonyloxyphenyl compounds. An example of this is a mixture (H1) consisting of equal amounts of the following such compounds:

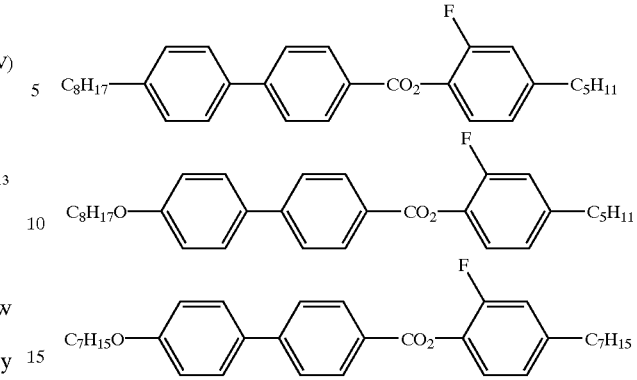

Another type of host material is based on a mixture (AS500) of the following dialkyldifluoroterphenyl compounds:

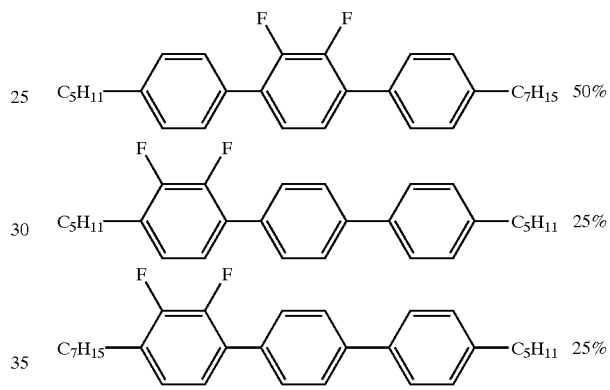

A further type of host material is based on a mixture of fluorinated phenylpyrimidines which may also contain at least one fluorinated terphenyl compound for enhancing the formation of a certain phase or phases in the liquid crystal composition. Examples of this type of host material are described in copending British Patent Application No. 9719822.0 filed on Sep. 17, 1997, whose disclosure is incorporated herein by reference. Particularly preferred is the host material utilised in Example 10 described therein.

The liquid crystal composition may further include other additives which are per se known in the art, for example for producing improved phase transitions, birefringence, viscosity and cone angle, memory angle and layer tilt.

According to a second aspect the present invention, there is provided a liquid crystal shutter comprising a pair of mutually spaced substrates upon which are provided respective opposed alignment surfaces which are spaced apart, and a layer of a liquid crystal composition according to said first aspect of the present invention filling the space between the alignment surfaces.

EXAMPLES AND DETAILED DESCRIPTION OF DRAWINGS

The present invention will now be described in further detail in the following Examples.

Example 1

Liquid crystal compositions using the host-material AS500 were formulated variously with the chiral dopant of the formula (V) above, the chiral dopant of the formula (III) above, and mixtures of such chiral dopants (V) and (III) in the respective relative proportions of 2:3, 3:2 and 1:1 by weight. The total chiral dopant concentration in each case was 5 wt %. The spontaneous polarisation Ps for each of the prepared liquid crystal compositions was evaluated at temperatures over a temperature range of −15 to +75° C.

Figure 1:
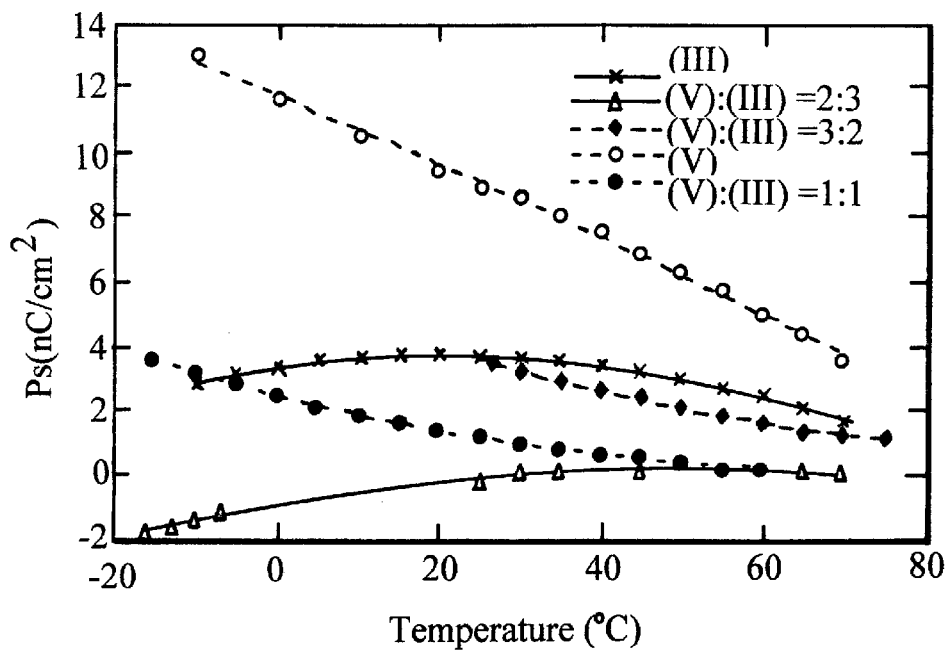
FIG. 1 is a graph in which spontaneous polarisation is plotted against temperature for various liquid crystal compositions containing single dopants and mixtures of two dopants.
Figure 2:
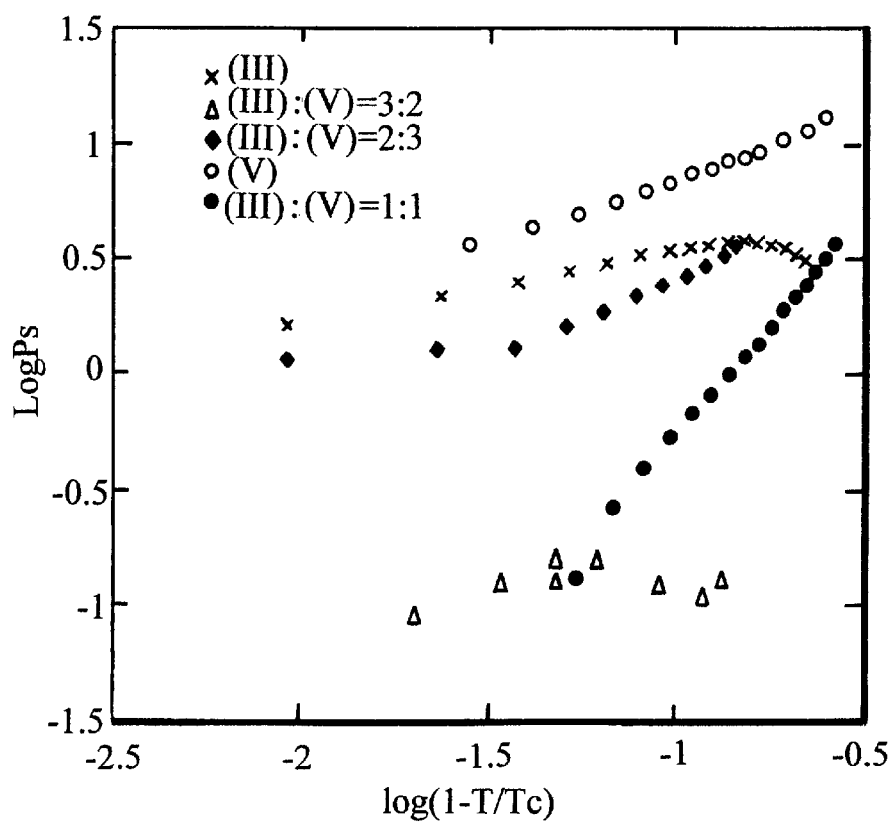
FIG. 2 is a graph in which log Ps versus log (1-T/Tc) is plotted for the same liquid crystal compositions.
Figure 3:
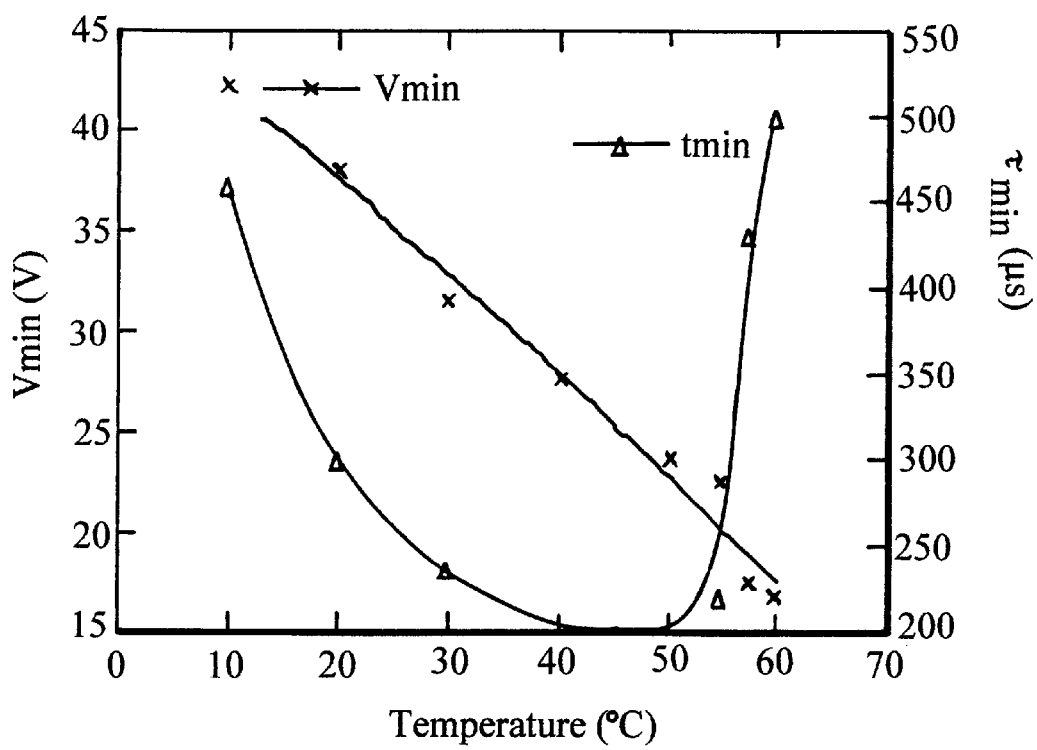
FIG. 3 is a τ-V plot of one of the liquid crystal compositions where the dopants are present in equal proportions.

The results obtained are set out in FIGS. 1 and 2. FIG. 2 indicates that the liquid crystal composition containing equal quantities of the chiral dopants (V) and (III) has the highest value of γ. The τ-V behaviour of such I:I mixture was determined and is illustrated in FIG. 3 where it can be seen that, initially, the rapid increase in spontaneous polarisation appears to compensate for the increase in viscosity on cooling, whilst $V_{min}$ rises with decreasing temperature.

Example 2

Figure 4:
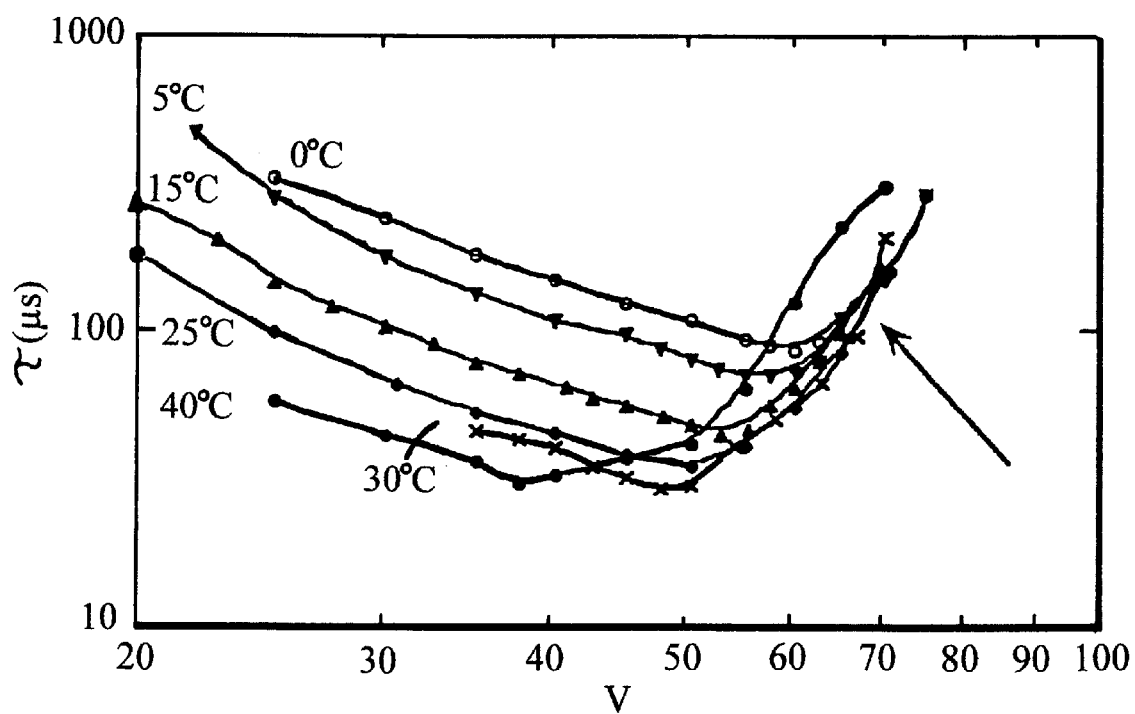
FIG. 4 is a graph of τ-V curves for a liquid crystal composition containing the same dopants in equal proportions but with a higher total chiral dopant concentration.

Equal quantities of the same chiral dopants ((III) and (V)) as used in Example 1 were used in a total chiral dopant concentration of 12% by weight in the host material AS500 referred to above, and τ-V curves were determined at temperatures between 0° C. and 40° C. The results are shown in FIG. 4 where it can be seen that there is a substantial overlap of the curves at 78V, thus indicating that a layer of such a composition in an optical shutter device can be addressed using substantially the same voltage and addressing time at any temperature within at least the 0° C. to 30° C. temperature range. At 40° C., pre-transitional effects shift the curve from the ideal position.

Example 3

Liquid crystal compositions using the host-material AS500 were formulated variously with the chiral dopant of the formula (V) above, the chiral dopant of the formula (IV) above, and mixtures of such chiral dopants (V) and (IV) in the respective relative proportions given in Table 1 below. The total chiral dopant concentration in each case was 5 wt %. The resultant compositions were evaluated for the following properties:

γ=temperature coefficient of spontaneous polarisation $Ps_0$=spontaneous polarisation at 1° below transition temperature to smectic C phase ($nC/cm_2$)

Tc—transition temperature to smectic C phase (° C.)

SmA Range=smectic A range (° C.) $Ps_{(Tc-30)}$.

The results obtained are listed in Table 1 below.

TABLE 1

| Dopant | Dopant Ratio | γ | $Ps_0$ | Tc | SmA Range | $Ps_{(Tc-30)}$ |
|---|---|---|---|---|---|---|
| (V):(IV) | 5:0 | 0.58 | −26.6 | 80 | 3 | −6.3 |
| (V):(IV) | 3:2 | 0.68 | −15.4 | 76.5 | 12.4 | −2.7 |
| (V):(IV) | 2.5:2.5 | 0.86 | −16.5 | 78.7 | 10.1 | −2.0 |
| (V):(IV) | 2:3 | 1.01 | −16.1 | 76.9 | 14.1 | −1.3 |
| (V):(IV) | 1:4 | @ | @ | 74.9 | 21 | @ |
| (V):(IV) | 0:5 | 0.28 | +2.9 | 73 | 20.8 | +1.45 |

(@ indicates that the property was unmeasurable due to tight pitch)

As can be seen from Table 1 above, the temperature coefficient (γ) of spontaneous polarisation for the chiral dopant mixtures is higher than that for the individual chiral dopants (V) and (IV).

Figure 5:
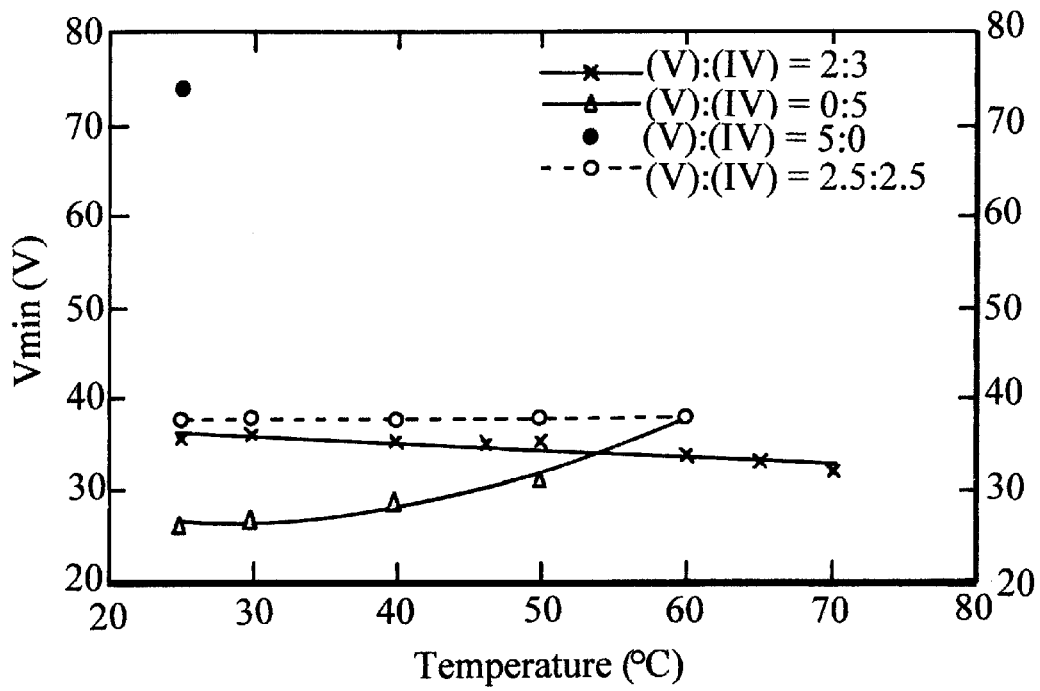
FIGS. 5 and 6 are graphs showing the $V_{min}$ and $\tau_{min}$ properties of other liquid crystal compositions.

FIG. 5 shows a plot of $V_{min}$ against temperature for certain of the compositions listed in Table 1 above from which it will be noted that the temperature dependence of $V_{min}$ is reduced as compared with the liquid crystal composition containing only chiral dopant (IV) and that the $V_{min}$ of such compositions is very much less than the liquid crystal composition containing only chiral dopant (V) whose $V_{min}$ is only indicated at 25° C.

Figure 6:
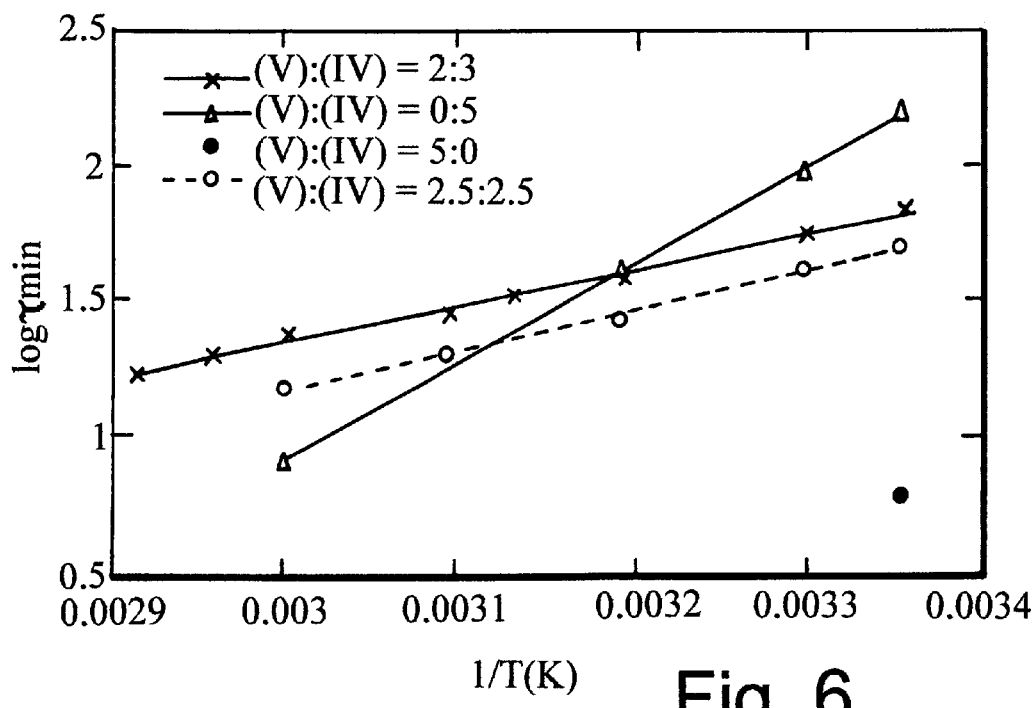

FIG. 6 is an Arrhenius plot of log $\tau_{min}$ against 1/T(K) for certain of the liquid crystal compositions listed in Table 1 above. As can be seen from FIG. 6, there is a reduced temperature dependence for certain of the liquid crystal compositions containing a mixture of the chiral dopants (V) and (IV).

Example 4

A series of liquid crystal compositions were formulated using the host material AS500 variously with the chiral dopant of formula (V) above, the chiral dopant of formula (II), and mixtures of such chiral dopants (V) and (II) in the respective relative proportions indicated in Table 2 below where the various properties of the liquid crystal compositions are also indicated in a similar manner to Table 1 above.

TABLE 2

| Dopant | Dopant Ratio | γ | $Ps_0$ | Tc | SmA Range | $Ps_{(Tc-30)}$ |
|---|---|---|---|---|---|---|
| (V):(II) | 5:0 | 0.58 | −26.6 | 80 | 3 | −6.3 |
| (V):(II) | 3:2 | 0.61 | −12.4 | 76.6 | 13.6 | −2.7 |
| (V):(II) | 2.5:2.5 | 0.77 | −13.6 | 76.5 | 14.7 | −2.1 |
| (V):(II) | 2:3 | 0.70 | −7.2 | 74 | 18 | −1.2 |

TABLE 2-continued

| Dopant | Dopant Ratio | Y | $Ps_0$ | Tc | SmA Range | $Ps_{(Tc-30)}$ |
|---|---|---|---|---|---|---|
| (V):(II) | 1:4 | @ | @ | 73.5 | 19.2 | @ |
| (V):(II) | 0:5 | 0.28 | 2.75 | 72 | 24 | +0.6 |

Here again, it can be seen that the temperature coefficient of spontaneous polarisation (γ) is increased in the liquid crystal compositions containing a mixture of the chiral dopants compared with those containing only one of the chiral dopants.

Example 5

A liquid crystal composition containing host material AS500 and 5 wt % of chiral dopant (III) and 5 wt % chiral dopant (VII) below was produced and tested.

(VII)

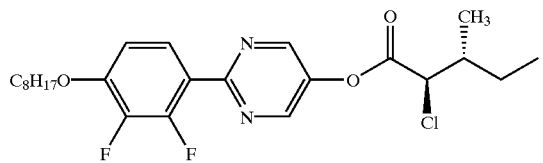

The composition exhibited a similar spontaneous polarisation to the equivalent composition containing 5 wt % chiral dopant (III) and 5 wt % chiral dopant (V). The temperature coefficient of spontaneous polarisation was also similar at 1.48.

Example 6

Further experiments were conducted using mixtures of chiral dopant (III) and one of the two isomeric chiral dopants (VIII) and (IX) below.

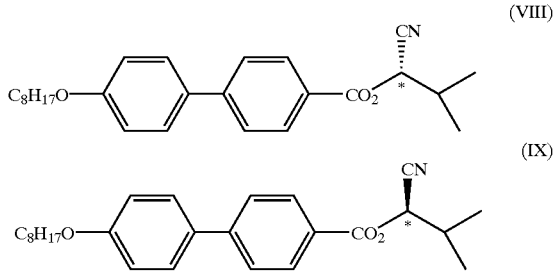

Chiral dopant (VIII) has a negative spontaneous polarisation, whilst chiral dopant (IX) has a positive spontaneous polarisation.

A liquid crystal composition comprising host material AS500, 2.3 wt % chiral dopant (IX) and 4.0% by weight chiral dopant (III) had a Ps at 25° C. of 9.8 and a γ of 0.39. Measurement of dV/dT gave no turn-around. A similar liquid crystal composition containing 2.3 wt % chiral dopant (VIII) and 4.0 wt % chiral dopant (III) had a Ps of 2.6, a γ of 0.9 and a dV/dT which was too slow to measure.

A similar liquid crystal composition to that described above but containing 2.8 wt % chiral dopant (VIII) and 4.0 wt % chiral dopant (III) had a Ps of 4.5 at 25° C., a γ of 0.77 and a dV/dT of 1.1. The increase of Ps in this latter mixture was found to be too much at higher temperatures and turn-around was not observed at temperatures above 50° C. when the Vmin was 75V and τ-min was 3.9 μs in a 1.5 μm cell.

To counteract this problem, a liquid crystal composition was prepared comprising AS500 host material, 1.3 wt % chiral dopant (VIII), 5.1 wt % dopant (III) and 2.1 wt % chiral dopant (V). Such composition had a γ of 1.3 and dV/dT of zero. Over the range 0 to 60° C., Vmin was 27.5 volts. τ-min was 53 μs at 25° C.

A further two liquid crystal compositions were prepared with the same three chiral dopants. A liquid crystal composition containing the host material AS500 and 2.0 wt % chiral dopant (VIII), 3.0 wt % chiral dopant (V) and 4.6 wt % chiral dopant (III) had a Ps of 7.3 at 25° C., a γ of 1.4 and exhibited no turn-around of dV/dT. A similar composition but containing 1.6 wt % chiral dopant (VIII), 3.3 wt % chiral dopant (V) and 5 wt % chiral dopant (III) had a Ps at 25° C. of 5.6, a γ of 1.0 and a dV/dT of 0.6.

Further liquid crystal compositions were formulated using host material AS500 and the dopants listed in Table 3 below.

TABLE 3

| Composit-ion | (VIII) wt % | (III) wt % | (V) wt % | γ |
|---|---|---|---|---|
| 1 | 1.6 | 4.0 | 1.0 | 0.51 |
| 2 | 1.9 | 2.3 | 1.6 | 0.77 |
| 3 | 2.0 | 2.5 | 2.5 | 0.67 |
| 4 | 2.0 | 2.0 | 3.0 | 0.61 |
| 5 | 2.0 | 0 | 0 | 0.5 |

As can be seen from the above, there was a marginal increase in γ for composition 1 as compared with composition 5 where the single chiral dopant (VIII) was employed. However, the other compositions 2, 3 and 4 showed a rather more substantial increase in γ.

Also, in Table 3 above:
For Composition 3, τ-V min at 25° C. is 23.2 μs at 50V in a 1.49 μm cell, and dV/dT=0.5.
For Composition 2, τ-V min at 25° C. is 61.4 μs at 22.5V in a 1.5 μm cell, and dV/dT=0.2.
For Composition 5, τ-V min at 25° C. is 20.0 μs at 26V in a 1.5 μm cell, and dV/dT=0.5.

Example 7

Chiral dopants (V) and (III) were utilised in liquid crystal compositions based on the host material disclosed in Example 10 of copending British Patent Application No. 9719822.0. The details of the chiral dopant concentrations and properties of such liquid crystal compositions are given in Tables 4 and 5 below.

TABLE 4

| Composition | Total dopant concentration (%) | Ratio (V):(III) | $T_{A-C}$ (° C.) | Ps (35° C.) nC/cm$^2$ | gamma |
|---|---|---|---|---|---|
| 1 | 10 | 6:4 | 56.0 | 3.71 | 0.91 |
| 2 | 10 | 5:5 | 56.7 | 2.45 | 0.96 |
| 3 | 10 | 4:6 | 55.6 | 1.0 | −0.59 |
| 4 | 14.8 | 8.9:5.9 | 50.8 | 5.8 | 0.73 |
| 5 | 16.1 | 9.7:6.4 | 49.4 | 6.3 | 0.69 |
| 6 | 20 | 11:8.9 | 42.5 | 5.85 | 0.85 |
| 7 | 20.2 | 12:8.2 | 45.4 | 7.5 | 0.76 |
| 8 | 22.1 | 13.5:8.6 | 41.9 | 8.74 | 0.69 |

TABLE 5

| Composition | Ps (35° C.) nC/cm² | $V_{min}$ (35° C.) | $\tau_{min}$ (35° C.) (µs) | dV/dT | Cell thickness (µm) |
|---|---|---|---|---|---|
| 1 | 3.71 | 25 | 21.0 | 0.16 | 1.31 (P132) |
| 2 | 2.45 | 17 | 70 | 0 | 1.28 |
| 3 | 1.0 | 16 | 200 | 0.5 | 1.49 (P132) |
| 4 | 5.8 | twisted | | N/A | 1.55 |
| 5 | 6.3 | 35 | 8.8 | 0.1 | 1.23 |
| 6 | 5.85 | 55 | 5.2 | 0.5* | 1.44 |
| 7 | 7.5 | 50 | 4.3 | 0.43 | 1.24 |
| 8 | 8.74 | No turn-around | | 0.8 | 1.5 |

*only measured at 25 and 35° C.

Of these compositions, Composition 5 above is of particular note with regard to its dV/dT, Vmin, τmin and Ps properties.

Example 8

The novel chiral dopant of formula (VI) above, being a difluorinated version of chiral dopant (V), was assessed. In AS500 host material, such chiral dopant gave a higher Ps per wt % (3.0) compared to 1.6 for chiral dopant (V) and a higher γ (0.7 compared with 0.6). A liquid crystal composition comprising the host material AS500, 4.88% chiral dopant (III) and 4.9 wt % chiral dopant (VI) gave a γ of 2.37.

Figure 7:
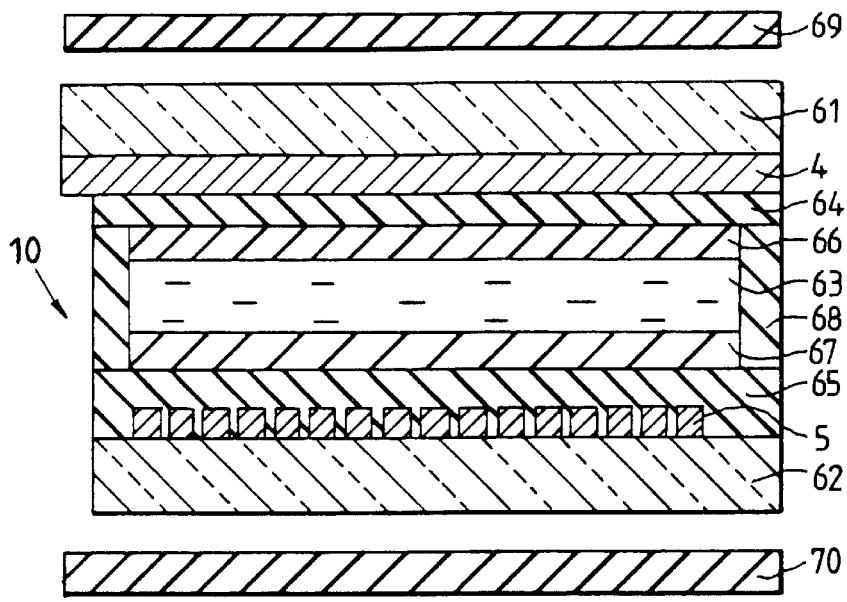
FIG. 7 is a cross-sectional view of a large ferroelectric liquid crystal display panel.

The following description will be given by way of example with reference to the large ferroelectric liquid crystal display (FLCD) panel shown diagrammatically in FIG. 7. The FLCD panel 10 comprises a layer 63 of ferroelectric liquid crystal composition according to the present invention contained between two parallel glass substrates 61 and 62 bearing first and second electrode structures on their inside surfaces. The first and second electrode structure comprise respectively a series of column and row electrode tracks 4 and 5 which cross one another at right angles to form an addressable matrix of modulating elements (pixels). Furthermore, alignment layers 66 and 67 are provided on insulating layers 64 and 65 applied on top of the column and row electrode tracks 4 and 5, so that the alignment layers 66 and 67 contact opposite sides of the ferroelectric liquid crystal layer 63 which is sealed at its edges by a sealing member or spacer 68. The panel 10 is disposed between polarisers 69 and 70 having polarising axes which are substantially perpendicular to one another. However, it will be understood that such a FLCD constitutes only one type of light modulating device to which the invention is applicable, and the following description of such a display is therefore to be considered as being given only by way of non-limiting example.

Figure 8:
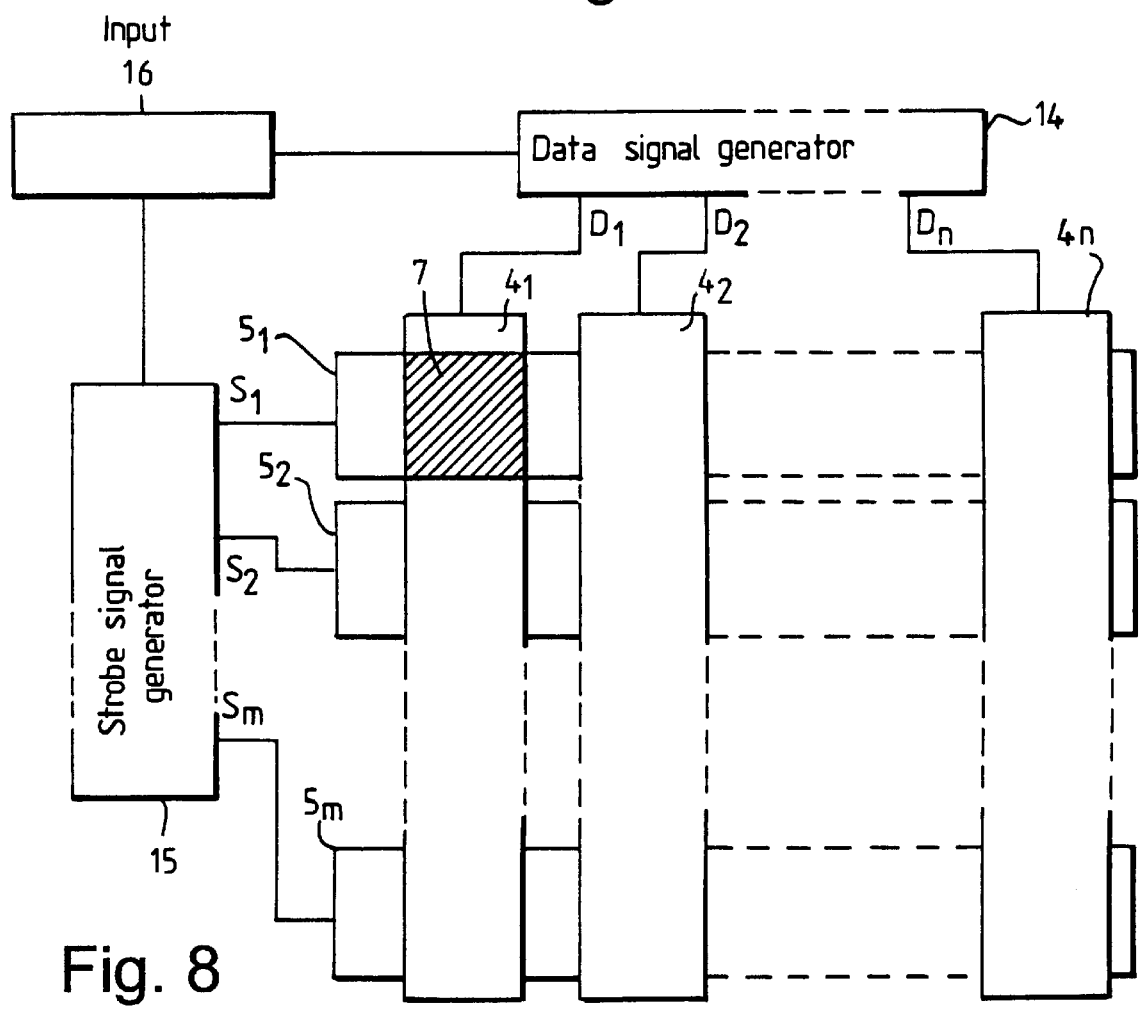
FIG. 8 is an addressing arrangement for the display panel of FIG. 7.

FIG. 8 diagrammatically shows an addressing arrangement for such a display panel 10 comprising a data signal generator 14 coupled to the column electrode tracks $4_1$, $4_2$, ... $4_n$ and a strobe signal generator 15 coupled to the row electrode tracks $5_1$, $5_2$, ... $5_m$. The addressable pixels 7 formed at the intersections of the row and column electrode tracks are addressed by data signals $D_1$, $D_2$, ... $D_n$ supplied by the data signal generator 14 in association with strobe signals $S_1$, $S_2$, ... $S_m$ supplied by the strobe signal generator 15 in response to appropriate image data supplied to the data signal generator 14 and clock signals supplied to the data and strobe signal generators 14 and 15 by a display input 16 which may incorporate spatial and/or temporal dither control circuitry for effecting spatial and/or temporal dither.

Figure 9:
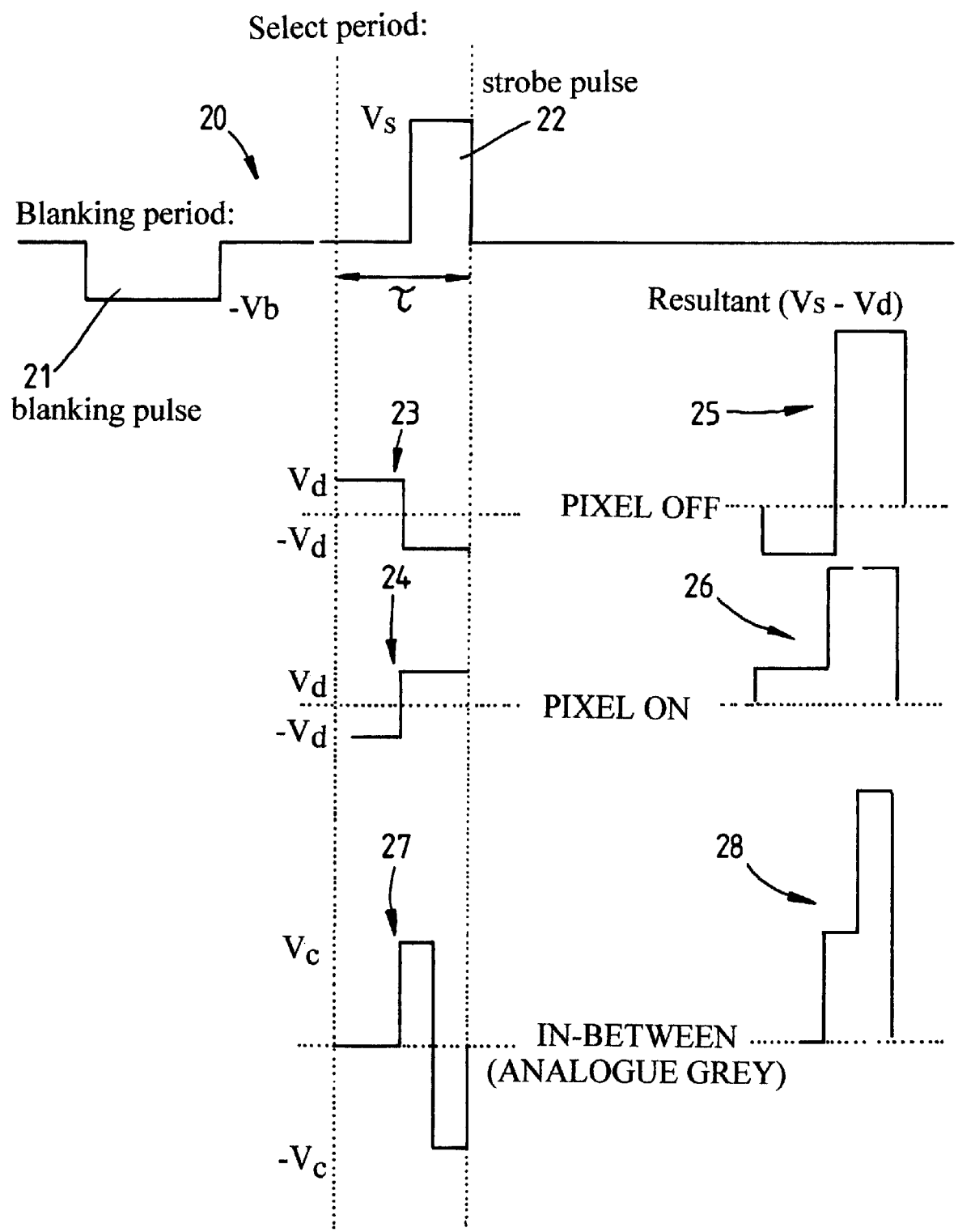
FIG. 9 is a diagram showing a typical strobe waveform used in the addressing arrangement of FIG. 8.
Figure 10:
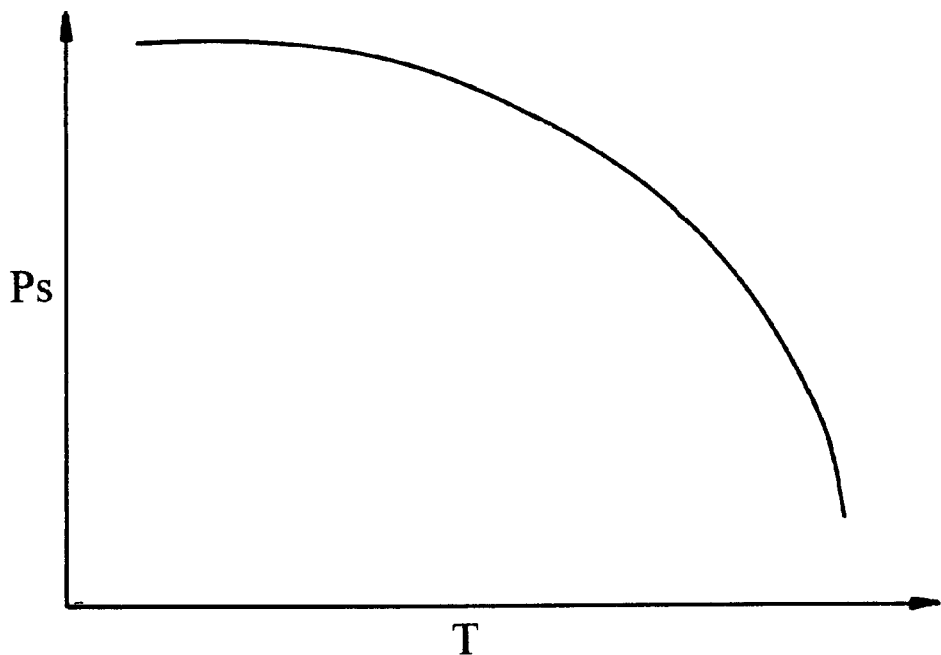
FIG. 10 is a graph showing spontaneous polarisation Ps plotted against temperature T for a known liquid crystal composition wherein the curve shown exaggerated for illustration.
Figure 11:
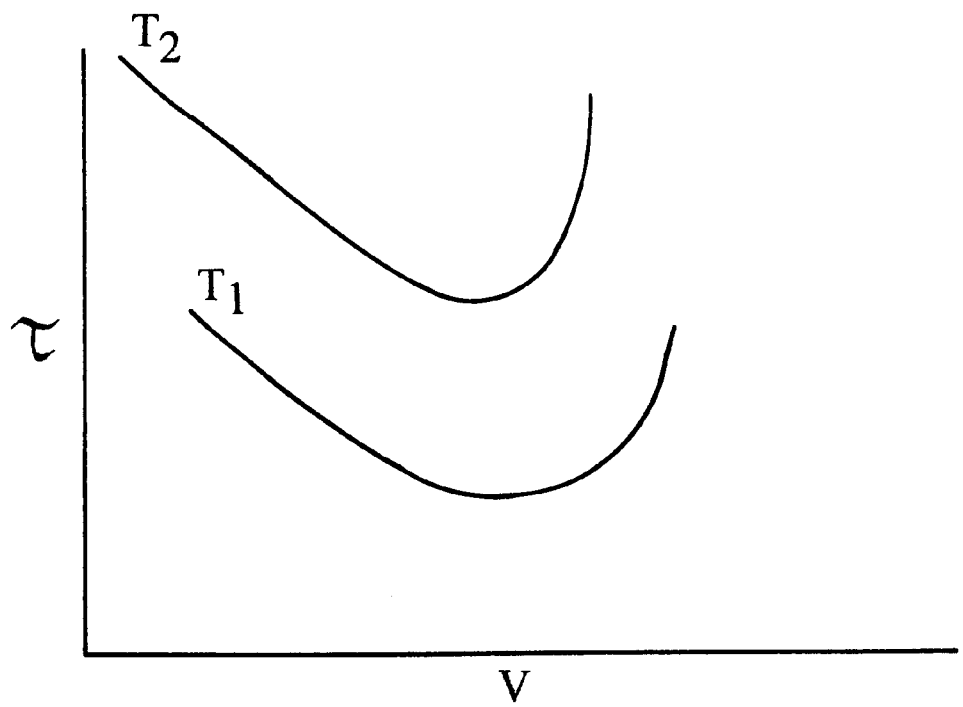
FIG. 11 is a graph showing typical $\tau$-$V_{min}$ curves at temperatures $T_1$ and $T_2$ for the known liquid crystal composition.
Figure 12:
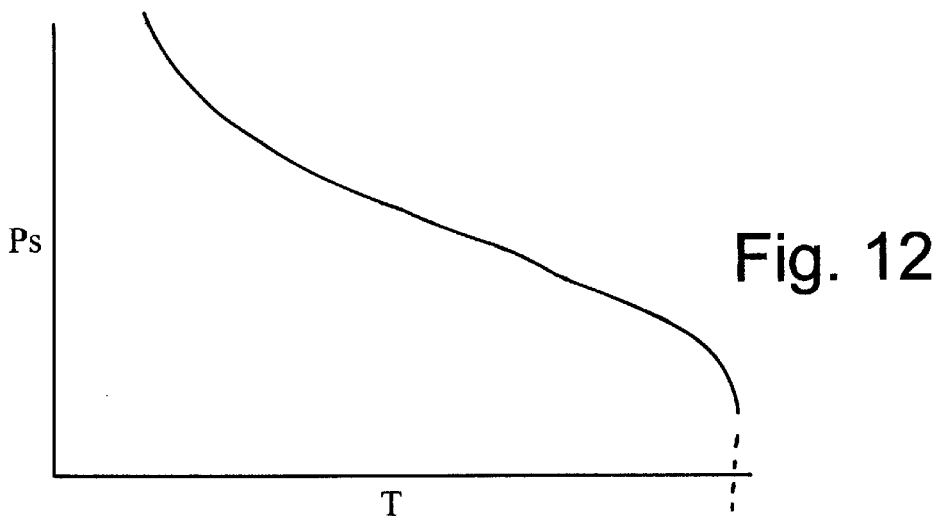
FIG. 12 is a graph similar to FIG. 10 for a liquid crystal composition according to the present invention.
Figure 13:
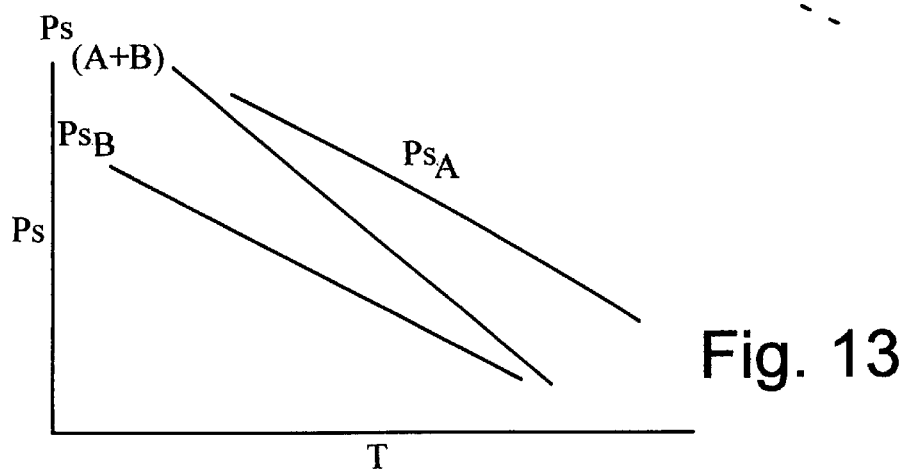
FIG. 13 is graph in which PS is plotted against T for liquid crystal compositions containing dopants A and B individually and dopants A and B together.
Figure 14:
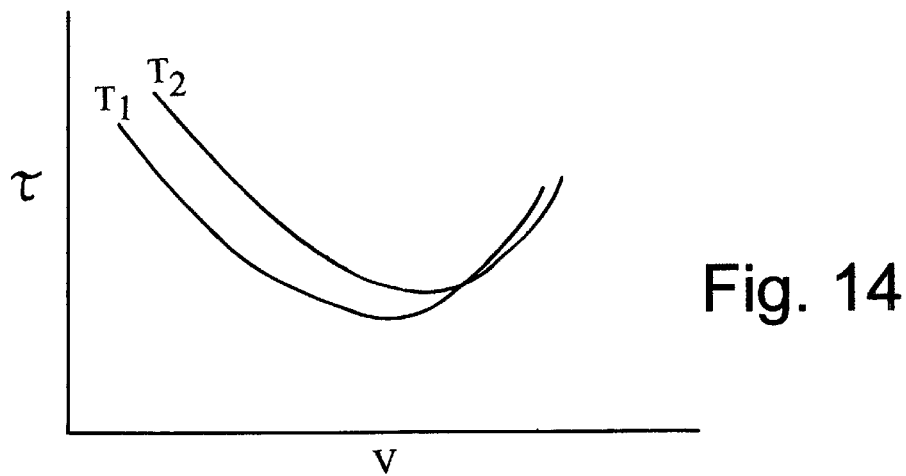
FIG. 14 is a graph similar to FIG. 11 for a liquid crystal composition according to the present invention.

The manner in which the waveforms of the data and strobe signals supplied to particular column and row electrode tracks determine the switching state of a pixel will now be briefly described with reference to FIG. 9 by way of non-limiting example. FIG. 9 shows a typical strobe waveform 20 comprising a blanking pulse 21 of voltage $-V_b$ in a blanking period and a strobe pulse 22 of voltage $V_s$ in a select period of duration τ, as well as a typical "off" data waveform 23 and a typical "on" data waveform 24 each comprising positive and negative pulses of voltage $V_d$ and $-V_d$. When the blanking pulse 21 is applied to the pixel, the pixel is switched to, or retained in, the normally black state or the normally white state independent of the data voltage applied to the column electrode track (the particular state being dependent on whether white or black blanking is applied). During the select period, the strobe pulse 22 is applied in synchronism with either the "off" data waveform 23 or the "on" data waveform 24 so that the resultant voltage across the pixel determines the state of the pixel and hence the transmission level. When the "off" data waveform 23 is applied, the resultant voltage 25 across the pixel causes the pixel to remain in the same state, that is the state to which the pixel has previously been blanked by the blanking pulse 21, and when the "on" data waveform 24 is applied, the resultant voltage 26 across the pixel causes the pixel to switch to the opposite state. Furthermore, an immediate data waveform 27, for example of the form shown in FIG. 9 having positive and negative pulses of voltage $V_c$ and $-V_c$ may be applied to the pixel producing a resultant voltage 28 across the pixel which causes the pixel to assume an intermediate state corresponding to an intermediate analogue grey level.

PREPARATION EXAMPLES

Example 1

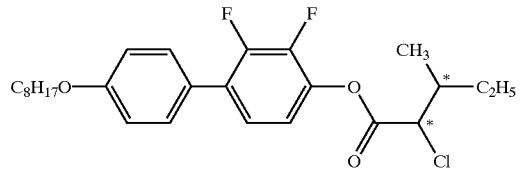

a. 2,3-Difluoro-4-hydroxy-4'-octyloxybiphenyl

A solution of n-butyllithium (1.60 ml, 10.0 M in hexanes, 0.016 mol) was added dropwise to a stirred, cooled (−78° C.) solution of 2,3-difluoro-4'-octyloxybiphenyl [see M. Hird and K. L. Toyne, *J. Mater. Chem.*, 1995, 5, 2239] (4.70 g, 0.015 mol) in dry THF (250 ml) under dry nitrogen. The mixture was stirred at −78° C. for 2 hr and a solution of trimethyl borate (3.15 g, 0.030 mol) in dry THF (10 ml) was added. The mixture was allowed to warm to room temperature overnight and a solution of 30% hydrogen peroxide (50 ml) in acetic acid (500 ml) was added dropwise at room temperature. The mixture was extracted into ether (3 times) and the combined ethereal extracts were washed with water and dried over $MgSO_4$. The solvent was removed in vacuo and the residue was recrystallised from ethanol to yield colourless crystals (3.45 g, 69%), mp 145° C.

$^1$H NMR ($CDCl_3$) δ0.90(3H, t), 1.30(8H, m), 1.45(2H, quint), 1.80(2H, quint), 4.05(2H, t), 5.20(1H, d), 6.84(1H, ddd), 6.97(2H,d), 7.07(1H, ddd), 7.52(2H, d); MS m/z 334(M⁺)

b. (2S, 3S)-2,3-Difluoro-4'-octyloxybiphenyl-4-yl-2-chloro-3-methylpentanoate

A solution of DCC (1.93 g, 9.37 mmol) in dry DCM (40 ml) was added dropwise to a stirred mixture of 2,3-difluoro- 4-hydroxy-4'-octyloxybiphenyl (2.72 g, 8.14 mmol), and (2S, 3S)-2-chloro-3-methylpentanoic acid [see T. Sierra, J. L. Serrano, M. B. Ros, A. Ezcurra, J. Zubia, *J. Am, Chem. Soc.,* 1992, 114, 7645] (1.23 g, 8.17 mmol) in dry DCM (200 ml) at room temperature under dry nitrogen. The mixture was stirred for 16 hours and the DCC was filtered off. The filtrate was washed successively with water, 5% acetic acid and water, and dried over $MgSO_4$. The solvent was removed in vacuo and the residue was purified by column chromatography (silica gel/DCM) to yield a colourless solid which was recrystallised from ethanol to yield colourless crystals (1.93 g, 51%), mp 40° C.

$^1$H NMR ($CDCl_3$) δ0.90(3H, t), 0.94(3H, t), 1.06(3H, d), 1.30(8H, m),1.35(1H, m), 1.45(2H, quint), 1.66(1H, m), 1.80(2H, quint), 2.11(1H, m), 4.05(2H, t), 4.23(1H,d), 6.97 (2H,d), 7.01 (1H,ddd), 7.20(1H, ddd), 7.56(2H, d); MS m/z 468($M^+$), 466($M^+$).

Example 2

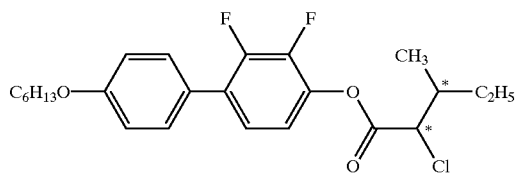

The above compound is produced by an analogous method to that described in Example 1 above.

What is claimed is:

1. A liquid crystal composition comprising a host material capable of exhibiting a smectic C phase, and a chiral dopant material which imparts or enhances chirality in the host material, said composition exhibiting temperature-dependent response time-operating voltage curves with a voltage minimum (τ-$V_{min}$ curves), wherein (a) the chiral dopant material comprises at least first and second chiral centres, (b) the chiral centres individually produce, in the liquid crystal composition, different and complementary temperature coefficients of spontaneous polarisation within a predetermined temperature range, and (c) the chiral centres are present in the liquid crystal composition in relative amounts such that regions of the τ-$V_{min}$ curves across the predetermined temperature range are substantially coincident.

2. A composition as claimed in claim 1, wherein the total amount of chiral dopant material is up to about 25% based on the total weight of the liquid composition.

3. A composition as claimed in claim 1, wherein the first chiral centre exhibits a spontaneous polarisation having an opposite sign to that of the second chiral centre.

4. A composition as claimed in claim 1, including at least one further chiral centre.

5. A composition as claimed in claim 1, wherein the first chiral centre is selected from those having a lactate moiety, and those located in an end group of a fluoroterphenyl compound.

6. A composition as claimed in claim 1, wherein the second chiral centre is provided by a Bahr-Happke C-series type dopant.

7. A composition as claimed in claim 1, wherein the first chiral centre is provided by a dopant of the formula (III):

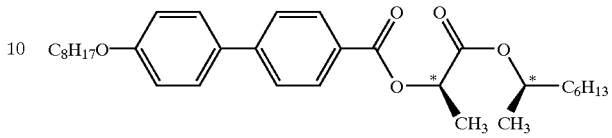

and the second chiral centre is provided by a compound of the formula (V) or (VI):

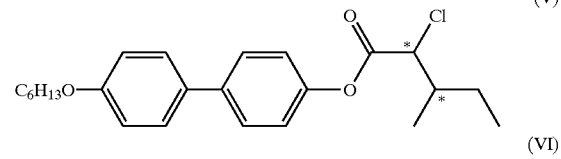

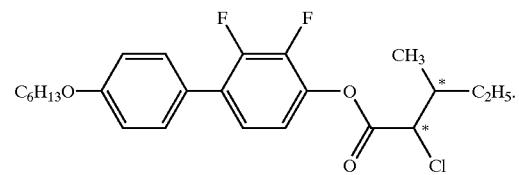

8. A composition as claimed in claim 1, wherein at least one of the chiral centres is provided in a compound containing a six membered aromatic ring.

9. A liquid crystal shutter comprising a pair or mutually spaced substrates upon which are provided respective opposed alignment surfaces which are spaced apart, and a layer of a liquid crystal composition as claimed in claim 1 filling the space between the alignment surfaces.

10. A compound of the formula (VI):

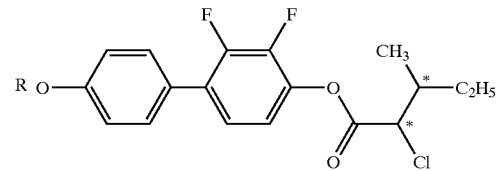

wherein R is an alkyl group of 6 to 8 carbon atoms.

* * * * *